(12) United States Patent
Tabor et al.

(10) Patent No.: US 8,344,172 B2
(45) Date of Patent: Jan. 1, 2013

(54) PREPARATION OF ANTIPLASTICIZERS FOR THERMOPLASTIC POLYESTERS

(75) Inventors: Rick Tabor, Glenview, IL (US); Brian K. Mirous, Evanston, IL (US); Timothy L. Lambert, Lindenhurst, IL (US); Michael E. O'Brien, Hainesville, IL (US); Matthew I. Levinson, Skokie, IL (US); Daniel J. Dershowitz, Columbus, OH (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 13/071,952

(22) Filed: Mar. 25, 2011

(65) Prior Publication Data

US 2012/0245268 A1    Sep. 27, 2012

(51) Int. Cl.
*C07C 69/76* (2006.01)
(52) U.S. Cl. .............. 560/8; 560/85; 560/54; 560/217
(58) Field of Classification Search .................. None
See application file for complete search history.

(56) References Cited

U.S. PATENT DOCUMENTS

| | | | |
|---|---|---|---|
| 3,557,167 A | 1/1971 | Hulsmann | |
| 4,003,877 A | 1/1977 | Lipson et al. | |
| 4,273,696 A | 6/1981 | Marshall et al. | |
| 4,474,918 A | 10/1984 | Seymour | |
| 4,705,844 A | 11/1987 | Espenschied | |
| 4,737,569 A | 4/1988 | Cawse | |
| 5,032,669 A | 7/1991 | Kantor | |
| 5,124,411 A | 6/1992 | Tang et al. | |
| 5,498,751 A | 3/1996 | Trapasso | |
| 5,552,512 A | 9/1996 | Sublett | |
| 2006/0275568 A1 | 12/2006 | Shi | |
| 2008/0113134 A1 | 5/2008 | Shi | |
| 2009/0087764 A1 | 4/2009 | Weiss | |
| 2009/0162589 A1 | 6/2009 | Buchanan et al. | |
| 2010/0143546 A1 | 6/2010 | Kriegel | |
| 2010/0143547 A1 | 6/2010 | Kriegel | |
| 2010/0233405 A1 | 9/2010 | Andrews | |

FOREIGN PATENT DOCUMENTS

WO    WO-82/00289    2/1982

OTHER PUBLICATIONS

International Search Report for PCT/US12/24554, dated May 25, 2012, 3 pages.

*Primary Examiner* — Yevegeny Valenrod
(74) *Attorney, Agent, or Firm* — Dilworth IP

(57) ABSTRACT

A process for making bis(aryloxyalkyl)terephthalates useful as antiplasticizers for thermoplastic polyesters is disclosed. Dimethyl terephthalate is reacted with an excess of an aryloxyalkanol in the presence of a condensation catalyst to produce an intermediate mixture comprising a bis(aryloxyalkyl)terephthalate, a mono(aryloxyalkyl)terephthalate, and unreacted aryloxyalkanol. This mixture continues to react at reduced pressure while unreacted aryloxyalkanol is removed and the mono-ester content is reduced to less than 1 mole % based on the combined amounts of mono- and bis-esters. Both steps are performed substantially in the absence of oxygen. Additional unreacted aryloxyalkanol is then removed to provide a purified bis(aryloxyalkyl)terephthalate having an overall purity of at least 98 mole % and a yellowness index less than 10. Careful control over catalysis, exposure to air, and other process conditions enables the preparation of high yields of bis(aryloxyalkyl)terephthalates that have low color and other valuable attributes. A method of producing bis(aryloxyalkyl)terephthalate articles having improved compressive strength is also disclosed.

30 Claims, No Drawings

US 8,344,172 B2

PREPARATION OF ANTIPLASTICIZERS FOR THERMOPLASTIC POLYESTERS

FIELD OF THE INVENTION

The invention relates to antiplasticizer additives for polymers, especially thermoplastic polyesters, and in particular, to a process for making bis(aryloxyalkyl)terephthalates having high purity and low color.

BACKGROUND OF THE INVENTION

Bis(aryloxyalkyl)terephthalates have been used to make adhesives, recording media, crystallization accelerators, and photosensitive layers. Recently, their use as gas-barrier additives for thermoplastic polyesters such as polyethylene terephthalate (PET) has been disclosed (see, e.g., U.S. Pat. Appl. Publ. Nos. 2010/0143546 and 2010/0143547). The additive functions as an antiplasticizer: it enhances modulus and tensile strength, thereby reducing creep when bottles are stacked. Additionally, it reduces the permeability of PET to carbon dioxide and oxygen, which improves the shelf life of carbonated beverages, particularly for smaller bottle sizes, and oxygen-sensitive drinks such as juice, tea products, or beer (see also U.S. Pat. Appl. Publ. No. 2006/0275568). As demonstrated in the '546 publication, adding just 3 wt. % of bis(2-phenoxyethyl)terephthalate increased barrier improvement factor by almost 20% and added about two weeks to shelf life. The process for making the bis(aryloxyalkyl) terephthalate is not discussed.

In a typical laboratory setting, bis(aryloxyalkyl)terephthalates are made by reacting terephthaloyl chloride with the corresponding aryloxyalkanol. For example, the reaction of terephthaloyl chloride with 2-phenoxyethanol in the presence of excess triethylamine and a solvent, followed by an organic workup to remove the ammonium salt, concentration, and recrystallization provides bis(2-phenoxyethyl)-terephthalate (see Scheme 1, compound 2 and Synthetic Examples 1 and 2 in U.S. Pat. Appl. Publ. No. 2009/0087764). Unfortunately, the lab procedure is impractical on a commercial scale because of the cost of terephthaloyl chloride and, among other issues, the need to recover a solvent and dispose of the ammonium salt.

In another laboratory approach (U.S. Pat. No. 3,557,167, Example 13), bis(2-phenoxyethyl)terephthalate is prepared by reacting diphenyl terephthalate with ethylene carbonate (1:3 molar ratio) in the presence of lithium chloride, followed by recrystallization from benzene. Limiting commercial use here are the need to synthesize diphenyl terephthalate (usually from terephthaloyl chloride), the relatively high cost of ethylene carbonate, and material losses when carbon dioxide is eliminated as a by-product.

Direct esterification of alcohols with terephthalic acid (TA) offers hope of a simpler purification by taking advantage of an acidic starting material and a neutral product. However, temperatures in excess of 250° C. (see, e.g., U.S. Pat. No. 4,737,569 or WO 82/00289) are normally required, and the potential ease-of-isolation advantages are undermined by the relatively poor solubility of TA compared with that of dimethyl terephthalate (DMT). Based on our own work, the approach may also impart unacceptably high color when the aryloxyalkanol is reacted with TA.

In one approach to making bis(aryloxyalkyl)terephthalates, the aryloxyalkanol is reacted with dimethyl terephthalate in the presence of a transesterification catalyst. Because the reaction is equilibrium controlled, it is difficult to convert substantially all of the DMT to a bis-ester, and the product can contain too much mono(aryloxyalkyl)terephthalate. An excess of the aryloxyalkanol can be used to shift the equilibrium toward completion. Unfortunately, side reactions can complicate this process, resulting in discoloration of the product. For a clear plastic bottle application, however, low color is important.

Additional problems result from the use of certain traditional condensation catalysts for the esterification. In particular, if residues from catalysts containing cobalt, manganese, cadmium, magnesium, and other metals are not avoided or thoroughly removed from the bis(aryloxyalkyl)terephthalates, they can cause an undesirable reduction in the molecular weight and intrinsic viscosity of the PET plastic into which the antiplasticizer is formulated, resulting in inferior blow-molded bottles (see U.S. Pat. Appl. Publ. No. 2006/0275568).

Some processes give low conversion to the desired bis-ester, while others generate the desired product, but in low yield or with too high an acid number, hydroxyl number, or moisture content. However, all of these considerations can be important when the bis(aryloxyalkyl)terephthalate is destined for making blow-molded PET bottles.

Yet another consideration is how easily the antiplasticizer can be processed uniformly with thermoplastics. Certain bis(aryloxyalkyl)terephthalates tend to be rather brittle, especially when produced at high purity and crystallinity. However, the antiplasticizer, when converted to pellets, prills, pastilles, flakes, granules or other articles, needs adequate crush strength so that it can be shipped or stored in gaylords, rail cars, tank trucks, or the like without disintegrating and forming dust. Moreover, when the antiplasticizer articles are combined with pellets of the thermoplastic polyester (e.g., PET), they should remain capable of shipping and storage without forming dust or separating from the dry-blended mixture.

In sum, bis(aryloxyalkyl)terephthalates are valuable antiplasticizers for thermoplastic polymers, especially PET, but a viable commercial synthesis is still needed. A suitable process would avoid pitfalls of a laboratory-scale process such as expensive starting materials, use of a solvent, and isolation/disposal of an ammonium salt. Preferably, the process would allow recycle and reuse of reactants and could be practiced using conventional esterification equipment and techniques. The process should avoid catalysts that reduce PET molecular weight during formulation into blow-molded articles. A valuable process would provide high yields of bis(aryloxyalkyl) terephthalates having the low color, low acid number, and low hydroxyl number needed to make the product acceptable for use as an antiplasticizer in the production of blow-molded thermoplastics. Ideally, the antiplasticizer could be formulated in a way that enables it to be stored and shipped without disintegrating, thereby ensuring an even distribution when it is combined and melt processed with thermoplastic polymers.

SUMMARY OF THE INVENTION

In one aspect, the invention relates to a process for making bis(aryloxyalkyl)terephthalates suitable for use as antiplasticizers for thermoplastic polyesters. The process comprises three steps. First, dimethyl terephthalate reacts with an excess of an aryloxyalkanol in the presence of a condensation catalyst comprising a Group 3, 4, 12, 13, 14, or 15 metal at a temperature less than the boiling point of the aryloxyalkanol to produce an intermediate mixture. The intermediate mixture comprises a bis(aryloxyalkyl)terephthalate, a mono(aryloxyalkyl)terephthalate, and unreacted aryloxyalkanol.

In a second step, the intermediate mixture continues to react at a temperature within the range of 180° C. to 250° C. under reduced pressure while unreacted aryloxyalkanol is removed. During this step, the mono(aryloxyalkyl)terephthalate content of the mixture is reduced to less than 1 mole % based on the combined amounts of mono- and bis-esters. At least the first two steps are performed substantially in the absence of oxygen.

In a third step, additional unreacted aryloxyalkanol is removed to provide a purified bis(aryloxyalkyl)terephthalate having an overall purity of at least 98 mole % and a yellowness index less than 10. We surprisingly found that careful control over catalysis, exposure to oxygen, and other process conditions are needed for making high yields of low-color bis(aryloxyalkyl)terephthalates that are valuable antiplasticizers for thermoplastic polymers.

In another aspect, the invention relates to a method of producing antiplasticizer articles. The method comprises melt blending a bis(aryloxy-alkyl)terephthalate with polyethylene terephthalate (PET) to give a polymer blend, and then forming antiplasticizer articles from the polymer blend. In this method, from 1 to 50 wt. % of PET is used based on the amount of polymer blend. The compressive strength of the articles is at least 25% greater than that of similar articles made from only the bis(aryloxyalkyl)terephthalate. The method provides articles that maintain their integrity during storage or shipping.

DETAILED DESCRIPTION OF THE INVENTION

In one aspect, the invention relates to a process for making a bis(aryloxyalkyl)terephthalate suitable for use as an antiplasticizer for a thermoplastic polyester.

Esterification

In a first step (a), dimethyl terephthalate reacts with an excess of an aryloxyalkanol in the presence of a particular condensation catalyst at a temperature less than the boiling point of the aryloxyalkanol (i.e., at 760 mm Hg) to produce an intermediate mixture comprising a bis(aryloxyalkyl)terephthalate, a mono(aryloxy-alkyl)terephthalate, and unreacted aryloxyalkanol.

Dimethyl terephthalate (DMT) is commercially available. DMT suitable for use in the process can come from any desired source. Because DMT is often synthesized from terephthalic acid (TA) or other TA derivatives, the most economical source of DMT may contain a low concentration of TA. We found with a spiking experiment (addition of 1 mol % TA to DMT) that DMT containing a substantial amount of TA performs well in the inventive process. Thus, the purity level of the DMT used is not considered critical. In particular, DMT containing up to 10 wt. % of TA is believed to be suitable for use in the process.

The DMT is reacted with an aryloxyalkanol. Suitable aryloxyalkanols have an aryloxy group, a divalent alkylene group, and a hydroxyl group. The aryloxy group has at least one benzene ring that is attached directly to an oxygen atom, and this oxygen atom is bonded to the divalent alkylene group. The aryloxy group can be substituted with alkyl, aryl, fused aryl, heterocyclyl, halogen, nitro, or other groups that do not interfere with the esterification reaction. Preferably, the aryloxy group is phenoxy or alkyl-substituted phenoxy. Most preferably, the aryloxy group is phenoxy. The divalent alkylene group links the aryloxy group to the hydroxyl group. It is linear, branched, or cyclic and preferably contains from 2 to 8 carbons, more preferably from 2 to 4 carbons. Thus, suitable aryloxyalkanols include, e.g., 2-phenoxyethanol, 2-(4-methylphenoxy)ethanol, 2-(4-chlorophenoxy)ethanol, 2-phenoxy-2-propanol, 4-phenoxycyclohexanol, and the like, and mixtures thereof. 2-Phenoxyethanol is most preferred.

Preferably, the aryloxyalkanol has a boiling point at atmospheric pressure greater than 210° C. Ideally, the aryloxyalkanol remains in the reaction mixture during esterification without the need for expensive pressurization.

An excess of the aryloxyalkanol is used. By "excess" we mean that enough aryloxyalkanol is used to react with substantially all of the dimethyl terephthalate present. Preferably, from 1.9 to 3.0, more preferably from 2.0 to 2.8, molar equivalents of the aryloxyalkanol are reacted with DMT. Along with removal of methanol, which forms as a by-product of esterification, use of an excess of the aryloxyalkanol helps to shift the equilibrium-controlled reaction in favor of the bis(aryloxyalkyl)terephthalate product.

A condensation catalyst is used to react DMT and the aryloxyalkanol. Suitable condensation catalysts are those capable of transesterifying DMT with the aryloxyalkanol to give a bis(aryloxyalkyl)terephthalate. While many kinds of catalysts will promote esterification, the catalyst used in the inventive process also cannot interfere with subsequent processing of the thermoplastic polyester into which the bis (aryloxyalkyl)terephthalate is added. It is known that certain elements, if present in the additive as catalyst residues, can reduce the molecular weight or intrinsic viscosity of the thermoplastic polyester when the polyester is melt processed (c.f., U.S. Pat. Appl. Publ. Nos. 2006/0275568 and 2010/0143546).

Thus, suitable condensation catalysts for use in the inventive process comprise a Group 3, 4, 12, 13, 14, or 15 metal, more preferably a Group 4 or 13 metal, and most preferably a Group 4 metal. Suitable catalysts comprise yttrium, lanthanum, titanium, zirconium, aluminum, gallium, germanium, antimony, tin, or zinc. More preferred catalysts comprise titanium or aluminum. Suitable catalysts include, for example, metal oxides, alkoxides, and carboxylates. Specific examples include tetra(ethoxy)titanium, tetra(n-propoxy)titanium, tetra(isopropoxy)titanium tetra(n-butoxy)titanium, tetra(isobutoxy)titanium, tetra(2-ethylhexoxy)titanium, tetra (n-butoxy)zirconium, tri(n-butoxy)aluminum, aluminum triacetate, germanium(IV) oxide, dibutyltin oxide, dibutyltin dilaurate, dibutyltin diacetate, and the like. Organotitanate catalysts, particularly tetra(alkoxy)titanium catalysts such as Tyzor® tetra(n-butoxy)titanium, a product of DuPont, are particularly preferred. Suitable catalysts are also available from Johnson-Matthey as Vertec® organic titanates.

In a preferred aspect, the catalyst is not moisture-sensitive. Suitable catalysts in this regard comprise a Group 12 metal, such as zinc carboxylates, particularly zinc acetate. Selection of such a catalyst obviates the need, on occasion, to remove moisture from the reactant mixture prior to charging the catalyst. Compare Example 5, below (zinc acetate catalyst is charged with water) with Example 1 (moisture is removed prior to charging a tetra(alkoxy)titanium catalyst).

The amount of condensation catalyst needed depends on the particular catalyst used, the particular aryloxyalkanol, the reaction conditions, scale, and other factors and is within the skilled person's discretion. Typically, the amount will be within the range of 1 to 1000 ppm, preferably from 10 to 500 ppm, based on the total amount of DMT and aryloxyalkanol used.

The esterification reaction is performed at a temperature less than the boiling point of the aryloxyalkanol. This prevents the aryloxyalkanol from being removed before it can react with the DMT. Preferably, the temperature is within the range of 100° C. to 250° C., more preferably from 130° C. to 230° C., most preferably from 150° C. to 220° C.

Surprisingly, we found that the bis(aryloxyalkyl)terephthalate can be made at relatively high temperature (e.g., 220° C.) without developing an unacceptable level of yellowness if oxygen is carefully excluded from the reaction mixture (see Example 1, below). Conversely, if oxygen is intentionally introduced, color development is rapid and significant (Comparative Examples 2 and 6A-6E). In general, if oxygen is not carefully excluded during esterification and subsequent removal of the aryloxyalkanol (i.e., during the first and second steps), the bis(aryloxyalkyl)-terephthalate can have a yellowness index that is unacceptably high for use in thermoplastic polyesters intended for blow-molded bottles.

As used herein, "substantially in the absence of oxygen" means that due care is exercised to minimize or eliminate opportunities for oxygen-containing gases, especially air, to come into contact with heated reaction mixtures during either of the first two steps of the claimed process. Thus, the reaction should be performed under an atmosphere of nitrogen, argon, or other inert or oxygen-free gas. When a partial vacuum is used during initial stripping, inert gas rather than air should be bled into the reactor. Other sources of air can include poor stirrer bearing seals, poorly sealed fittings, or the like. The skilled person will be aware of other possible sources of air leaks, which will depend largely on the particular equipment chosen for performing the first and second steps.

Optionally, the esterification is performed in the presence of an antioxidant. Suitable antioxidants include phenolic antioxidants, organophosphorus compounds, lactones, or the like. Many antioxidants are commercially available from BASF and other suppliers. For examples of suitable antioxidants, see U.S. Pat. Appl. Publ. No. 2010/0233405, the teachings of which are incorporated herein by reference, and references cited therein.

The intermediate mixture resulting from initial reaction step (a) comprises a bis(aryloxyalkyl)terephthalate, a mono(aryloxyalkyl)terephthalate, and unreacted aryloxyalkanol. Normally, the mixture also includes methanol, which is eliminated in the esterification. Preferably, at least 90%, more preferably at least 95%, of the dimethyl terephthalate reacts in the initial reaction step. It is not necessary, however, that all of the DMT be converted to the bis(aryloxyalkyl)terephthalate (also called "bis-ester") at this stage. Normally, a substantial proportion of the mono(aryloxyalkyl)terephthalate ("monoester" or "half ester") remains. Preferably, from 65 to 85 mole %, more preferably from 70 to 80 mole %, of the dimethyl terephthalate is converted to the bis(aryloxyalkyl)terephthalate, with most of the balance (typically 15 to 35 mole %) being converted to the mono-ester. While it is tempting to push conversion to the bis-ester to a high level during the initial reaction step, milder conditions, including lower temperature, may help to ensure an acceptably low color in the intermediate mixture and purified bis(aryloxyalkyl)-terephthalate.

Continued Esterification with Aryloxyalkanol Removal

In a second step (b), reaction of the intermediate mixture continues at a temperature within the range of 180° C. to 250° C. while unreacted aryloxyalkanol is removed under reduced pressure. During this step, the mono(aryloxyalkyl)-terephthalate content of the mixture is reduced to less than 1 mole % based on the combined amounts of mono- and bis-esters.

As in the first step, temperature control in the second step is not critical for isolating a purified bis(aryloxyalkyl)terephthalate having a desirably low yellowness index provided that oxygen is carefully excluded. Thus, this second process step is also performed substantially in the absence of oxygen. Preferably, the temperature for this step is within the range of 150° C. to 250° C., more preferably from 175° C. to 230° C., and most preferably from 185° C. to 220° C.

As noted earlier, the aryloxyalkanol is used in excess in the esterification reaction. Thus, unreacted aryloxyalkanol needs to be removed from the intermediate mixture. This removal is accomplished by heating under reduced pressure. Preferably, a gentle vacuum (e.g., 700-550 mm Hg) is applied, which assists in removal of mostly methanol. Usually, the vacuum is gradually improved (e.g., from 550 mm to 20 mm Hg), typically at or near the desired maximum temperature, to remove most of the aryloxyalkanol. The pressure can be further reduced if desired to remove a greater proportion of the unreacted aryloxyalkanol.

Heating under vacuum in step (b) removes much of the aryloxyalkanol from the intermediate mixture. Coincidentally, most of the mono(aryloxyalkyl)-terephthalate present after the initial esterification reacts with aryloxyalkanol and is converted to the desired bis-ester. Thus, the reaction is continued until the mono(aryloxyalkyl)terephthalate content of the mixture is reduced to less than 1 mole %, preferably less than 0.5 mole %, based on the combined amounts of mono- and bis-esters.

It is often helpful to include an inert gas purge along with heating and vacuum to assist in removal of unreacted aryloxyalkanol. The inert gas can be nitrogen, argon, or the like. As noted above, oxygen-containing gases such as air are excluded during this step. Typically, the flow of inert gas is adjusted to achieve the desired reduction in pressure. Thus, if vacuum is improved, a corresponding decrease in the amount of inert gas purge will be applied. The unreacted aryloxyalkanol is valuable and is, of course, preferably recovered and reused.

Additional Removal of Aryloxyalkanol

In a third step (c), additional unreacted aryloxyalkanol is removed to provide a purified bis(aryloxyalkyl)terephthalate having an overall purity of at least 98 mole % and a yellowness index less than 10.

This step is used to reduce the aryloxyalkanol content of the bis(aryloxyalkyl)-terephthalate to a level that is acceptable for antiplasticizer applications. Typically, the bis(aryloxyalkyl)terephthalate, following completion of step (b), will contain up to 5 mole % of residual aryloxyalkanol. For commercial use, however, the bis(aryloxyalkyl)terephthalate needs to have an overall purity of at least 98 mole %. Preferably, it also contains less than 1 mole %, more preferably less than 0.5 mole %, and most preferably less than 0.25 mole % of the aryloxyalkanol.

In one suitable approach, in-situ stripping of the product from step (b) under vacuum, preferably with an inert gas purge, is used to further reduce the aryloxyalkanol content. It remains important to perform an elevated temperature strip substantially in the absence of oxygen. Temperature is preferably within the range of 130° C. to 230° C., most preferably from 150° C. to 210° C. Typically, the pressure is reduced to below 20 mm Hg for this step, preferably to below 10 mm Hg.

In another suitable approach, the product is removed from the esterification reactor and is subjected to vapor (methanol, water, etc.) and/or inert gas stripping, wiped-film evaporation, steam stripping, fractional melt crystallization, solvent crystallization, or other similar techniques until the aryloxyalkanol content has been reduced to an acceptable level. Methods that permit recovery and reuse of the aryloxyalkanol are preferred.

Purified bis(aryloxyalkyl)terephthalate

The purified bis(aryloxyalkyl)terephthalate has a yellowness index less than 10. This is the maximum tolerable yellowness index for the targeted application in blow-molded articles, particularly blow-molded PET bottles. Preferably, the yellowness index is less than 5, and more preferably it is less than 2. Numerous factors—some known, some unknown—contribute to the development of yellow color in the bis(aryloxyalkyl)terephthalate.

Yellowness index is normally measured using a color spectrophotometer. A suitable technique is described in more detail in the experimental section below. Powder samples can be analyzed using an instrument such as a ColorQuest XE spectrophotometer, which is available from HunterLab. Samples are conveniently prepared by pulverizing a purified bis(aryloxyalkyl)terephthalate sample to a fine powder, spreading the sample to form a relatively uniform layer, and analyzing as described below. A standard method (ASTM E313-10) is used to calculate yellowness index.

For applications that demand a bis(aryloxyalkyl)terephthalate having exceptionally low yellowness index (e.g., less than 5), it may be helpful to treat the purified material with an adsorbent to further reduce its yellowness index. Suitable adsorbents include Magnesol® adsorbent (magnesium silicate, product of Dallas Group of America), activated carbons or charcoal, diatomaceous earth, aluminas, clays, silicas, titanias, magnesias, and the like, or combinations thereof. We found that, on a weight basis, Magnesol adsorbent is particularly effective in reducing yellowness index in a purified bis(aryloxyalkyl)terephthalate. See Examples 3F-3H below, where as little as 1 wt. % Magnesol adsorbent reduced yellowness index from about 8 to less than 2.

In addition to yellowness index, the purified bis(aryloxyalkyl)terephthalate preferably meets other specifications that may be important depending on the targeted application. For instance, the hydroxyl number of the bis(aryloxyalkyl)terephthalate is preferably less than that of the thermoplastic polyester with which it is to be combined. More preferably, the hydroxyl number is less than 1 mg KOH/g, most preferably less than 0.5 mg KOH/g. The acid number can also be important. Preferably, the acid number of the purified bis(aryloxyalkyl)terephthalate is less than that of the thermoplastic polyester with which it is to be combined. More preferably, the acid number is less than 1 mg KOH/g, most preferably less than 0.5 mg KOH/g. If either the hydroxyl number or the acid number is too high, there may be an undesirable impact on how the thermoplastic polyester (into which the antiplasticizer is formulated) processes.

The purified bis(aryloxyalkyl)terephthalate has an overall purity of at least 98 mole %, preferably at least 99 mole %, and most preferably at least 99.5 mole %. Thus, the total amount of DMT, aryloxyalkanol, and mono-ester present in the purified bis(aryloxyalkyl)terephthalate will not exceed 2 mole %, and preferably will not exceed 1 mole %. Any convenient method of determining overall purity can be used, such as liquid chromatography, gel permeation chromatography, mass spectrometry, infrared spectroscopy, $^1$H or $^{13}$C NMR spectroscopy, or the like, or combinations of these techniques.

In a preferred aspect, the aryloxyalkanol is 2-phenoxyethanol, and the resulting bis(aryloxyalkyl)terephthalate is bis(2-phenoxyethyl)terephthalate, also known as "PEM." PEM has proved to be a valuable antiplasticizer additive for thermoplastic polyesters, particularly PET. As shown in U.S. Pat. Appl. Publ. No. 2010/0143546, the teachings of which are incorporated herein by reference, adding just 3 wt. % of PEM into a PET formulation can increase barrier improvement significantly and add weeks to bottle shelf life.

The purified bis(aryloxyalkyl)terephthalate is preferably converted into a form that facilitates its combination and blending with a thermoplastic polyester. The post-manufacture treatment may comprise pelletizing, flaking, granulating, pastillating, prilling, spray drying, or other well-known techniques. The bis(aryloxyalkyl)terephthalate can be converted either in pure form or as masterbatch with a portion of the thermoplastic polyester into which it will ultimately be compounded. If desired, fillers or other additives can be included in the purified bis(aryloxyalkyl)terephthalate to make it more suitable for shipping or handling for a particular use.

Method of Producing Antiplasticizer Articles

The invention includes a method of producing antiplasticizer articles. In this method, a bis(aryloxyalkyl)terephthalate is first melt blended with polyethylene terephthalate (PET) to give a polymer blend. Any desired means can be used to melt blend the PET and bis(aryloxyalkyl)terephthalate. Antiplasticizer articles are then formed from the polymer blend. Techniques used to form the articles are well known, and include pelletizing, pastillating, prilling, flaking, granulating, and the like. The amount of PET used is from 1 to 50 wt. %, more preferably from 5 to 25 wt. %, most preferably from 10 to 25%, based on the amount of polymer blend.

We surprisingly found that such articles (typically in the form of pellets, flakes, granules, pastilles, prills, or tablets) have a compressive strength as measured by ASTM D-1621, that is at least 25% greater than that of similar articles made from only the bis(aryloxyalkyl)terephthalate (see Example 8 and Comparative Example 9). The bis(aryloxyalkyl)-terephthalates, when produced at high purity, can be brittle and prone to disintegration during storage or shipping. On the other hand, the articles require integrity if they are to be formulated effectively with other thermoplastic materials, such as PET pellets. The inventive method affords bis(aryloxyalkyl)-terephthalate antiplasticizers that meet this requirement. Because of their improved compressive strength, the antiplasticizers can be stored and shipped in gaylords, rail cars, tank trucks, or the like with minimal disintegration and dust formation. Moreover, when the antiplasticizer articles are combined with pellets of the thermoplastic polyester (e.g., PET), they can be shipped, stored, and processed without forming dust or separating from the dry-blended mixture. This ensures the antiplasticizer will be evenly distributed when the mixture is melt processed.

The following examples merely illustrate the invention. Those skilled in the art will recognize many variations that are within the spirit of the invention and scope of the claims.

Yellowness Index

A ColorQuest XE spectrophotometer (HunterLab) is used to analyze powder samples of PEM to determine a yellowness index.

Sample preparation: A solid sample (10-15 g) of PEM is ground in a porcelain mortar for 2 min. and transferred to a 60×15 mm petri dish, which is tapped gently on the lab countertop three times to evenly distribute the powder.

Instrument conditions: Mode: reflectance specular included (RSIN); aperture: 1.00 in.; UV filter position: normal; illuminant: D65/10. Each sample is scanned in three different locations, and the data is averaged.

Calculation of yellowness index: by ASTM E313-10.

Example 1

Preparation of Bis(2-phenoxyethyl)terephthalate ("PEM")

A 5-L round-bottom flask equipped with overhead stirrer, thermocouple, and nitrogen sparge tube is connected to an ice-water cooled vacuum condenser and receiver flask. The reactor is charged with dimethyl terephthalate, "DMT" (874 g, 4.5 mol, from Alfa Aesar) and 2-phenoxyethanol, "2-PE" (1679 g, 12.2 mol, product of Dow Chemical). The reactor is heated to 110° C. to 120° C. to dissolve the DMT in the 2-PE. The stirrer is set for 200 rpm, and the reaction mixture is held at 110° C. to 120° C. for 15-30 min. under a nitrogen sparge (140 mL/min) to remove moisture. Tyzor® tetra(n-butoxy) titanium catalyst (0.73 g, ~300 ppm based on total reactants, product of DuPont) is added to the reactor, and the contents are heated to 140° C. Distillate, predominantly methanol, is collected as the temperature is slowly increased in steps to 220° C. Thereafter, a gentle vacuum is applied. The pressure is slowly reduced (to 10 mm Hg) with a concurrent reduction in nitrogen sparging, and additional distillate, predominantly 2-phenoxyethanol, is collected. The product, clear with a yellow tint, is cooled and recovered to give crystals with a slight cream color. At this point, further purification may be used to remove additional 2-PE and other impurities.

Gas chromatography analysis of the PEM product: 98.9% PEM, 0.0% DMT, 0.1% mono(2-phenoxyethyl)terephthalate, 1.0% 2-PE. Yellowness index: 1.01; acid number (by titration in acetone to a phenolphthalein endpoint): 0.02 mg KOH/g.

COMPARATIVE EXAMPLE 2

The procedure of Example 1 is generally repeated, except that an air leak is introduced that prevents the vacuum from being lowered below 45 mm Hg.

Yellowness index: 8.93; acid number: 0.03 mg KOH/g.

EXAMPLES 3A-3H

Effect of Adsorbents on Yellowness Index

PEM having a relatively high color (yellowness index=8.4) is treated with various adsorbents in an attempt to remove color. Thus, eight 4-oz. jars, each containing PEM (50 g), are placed in an oven at 130° C. to melt. A second set of jars containing Magnesol® D60 adsorbent (magnesium silicate, product of Dallas Group of America), carbon black (Nuchar), and diatomaceous earth (Fisher Scientific) are also placed in the oven. Glass powder funnels containing a folded cone of Whatman 42 filter paper are placed on top of Erlenmeyer flasks, and these are also put into the oven. Once the PEM samples have melted, the adsorbents are added to the PEM and swirled 30 seconds to ensure good mixing. The samples are then filtered. About 15 g of PEM filters through over 45 minutes. The filtrates are analyzed for color and acid number. Results appear in Table 1.

The results demonstrate that PEM color can be further reduced using adsorbents. Diatomaceous earth is generally ineffective. Based on the amounts of adsorbent needed to achieve a desirably low color, Magnesol outperforms carbon black, giving PEM of very low color even with only 1 wt. % adsorbent.

TABLE 1

Effect of Adsorbents on Yellowness Index

| Ex. | Adsorbent (wt. %) | Acid # (mg KOH/g) | Yellowness index |
|---|---|---|---|
| 3A | None (control) | 0.09 | 8.36 |
| 3B | Diatomaceous earth (10%) | 0.08 | 5.89 |
| 3C | Carbon black (1%) | 0.12 | 4.49 |
| 3D | Carbon black (5%) | 0.09 | 2.18 |

TABLE 1-continued

Effect of Adsorbents on Yellowness Index

| Ex. | Adsorbent (wt. %) | Acid # (mg KOH/g) | Yellowness index |
|---|---|---|---|
| 3E | Carbon black (10%) | 0.08 | 1.07 |
| 3F | Magnesol (1%) | 0.07 | 1.48 |
| 3G | Magnesol (5%) | 0.06 | 1.13 |
| 3H | Magnesol (10%) | 0.09 | 1.16 |

Example 4

Effect of Added Terephthalic Acid

The procedure of Example 1 is generally followed, except that 1.0 mol % of terephthalic acid, based on the amount of DMT charged, is included in the reactor charge. Yellowness index: 1.47; acid number: 0.00 mg KOH/g.

The example demonstrates TA is esterified in the process, and that mixtures of DMT and TA can be used to manufacture PEM having acceptable properties for use as an antiplasticizer.

Example 5

Zinc Acetate as a Catalyst in a High-Moisture Esterification

The procedure of Example 1 is generally followed to make PEM with the adjustments indicated. First, zinc acetate (1.35 g) replaces tetra(n-butoxy)titanium as the catalyst. The initial reactor charge includes the zinc acetate and deionized water (122 g). (Zinc acetate is compatible with water, while the titanium catalyst is not.) The maximum temperature is 200° C. The product is slightly cloudy, but yields very white crystals with an acid number of 0.03 mg KOH/g.

The example demonstrates that a high moisture content in the reaction mixture can be tolerated well if a condensation catalyst comprising a Group 12 metal is selected. This obviates the need to remove traces of moisture from the reactants before charging the catalyst.

COMPARATIVE EXAMPLES 6A-6E

Air Sparging

A slight vacuum is applied to a reactor containing molten PEM at 195° C. so that it pulls a small stream of air through a metal dip tube and into the PEM. Samples of PEM are periodically removed from the reactor and immediately cooled before being analyzed for yellowness index.

TABLE 2

Effect of Air Sparging on Yellowness Index

| Ex. | Total sparge time (min.) | Yellowness index |
|---|---|---|
| 6A | 0 | 6.12 |
| 6B | 20 | 11.23 |
| 6C | 40 | 13.11 |
| 6D | 60 | 14.49 |
| 6E | 120 | 16.49 |

Comparative Examples 6A-6E demonstrate the importance of excluding oxygen, especially in the early portion of the experiment, for making PEM having low color.

Example 7

Preparation of a Melt Blend of PET in PEM

Bis(2-phenoxyethyl)terephthalate ("PEM," 100 g) is heated with stirring at 190° C. until molten. Bottle-grade polyethylene terephthalate (PET, 5 g) is added, and the temperature is gradually increased until the PET becomes soluble (about 225° C.). Additional PET is added in 5-g increments to the stirred mixture at 230° C. over several hours. Some darkening occurs during the course of the additions, and a total of 30 g of PET (23.1 wt. % based on the combined amount of PET+PEM) is added. The final product is transferred to a Teflon dish, and it cools to form an off-white cake. The polymer blend is less friable and more breakage-resistant than pure PEM.

Example 8

Pellets from a 20 wt. % PET in PEM Blend

PEM (169.3 g) is heated in a 500-mL flask equipped with a thermocouple, mechanical stirrer, and nitrogen atmosphere. When the temperature reaches 230° C., bottle-grade polyethylene terephthalate (PET, 42.3 g) is added to the molten PEM in three portions while allowing each portion to dissolve before adding the next. After about 1.5 h, all of the PET has dissolved to provide a blend containing 20 wt. % PET. The resulting blend is poured into 1"-diameter, flat-bottom scintillation vials to half-fill each vial. The vials are allowed to cool overnight. Each vial is scored with a diamond-tipped pen and carefully fractured with a small hammer to recover the resulting polymer "pellet." The top surface of each pellet is removed by abrasion with 80-grit sandpaper to provide a flat surface. The pellets, which average 0.98" in diameter and 0.73" tall, are submitted for physical testing. Compressive strength (avg., by ASTM D-1621): 453 psi. Friability (avg. weight loss, by tumbling, ASTM C-421): 47%.

COMPARATIVE EXAMPLE 9

The procedure of Example 8 is generally followed except that PET is omitted. Thus, PEM is simply heated until molten and transferred to the scintillation vials to form pellets. Compressive strength (avg.): 153 psi. Friability (avg. wt. loss): 96%.

Example 8 and Comparative Example 9 demonstrate the improved compressive strength and friability of PEM compositions that incorporate PET. The results suggest that pellets, pastilles, tablets, or other articles of PEM formulated to contain up to 20 wt. % PET will have advantages compared with PEM alone for shipping, storage, and formulation into PET.

The preceding examples are meant only as illustrations; the following claims define the invention.

The invention claimed is:

1. A process for making a bis(aryloxyalkyl)terephthalate suitable for use as an antiplasticizer for polymers, comprising the steps of:
    (a) reacting dimethyl terephthalate with from 1.9 to 3.0 molar equivalents of an aryloxyalkanol in the presence of a condensation catalyst comprising a Group 3, 4, 12, 13, or 15 metal at a temperature less than the boiling point of the aryloxyalkanol to produce an intermediate mixture comprising a bis(aryloxyalkyl)terephthalate, a mono(aryloxyalkyl)terephthalate, and unreacted aryloxyalkanol;
    (b) continuing to react the intermediate mixture at a temperature within the range of 150° C. to 250° C. under reduced pressure while removing unreacted aryloxyalkanol and reducing the mono(aryloxyalkyl)terephthalate content of the mixture to less than 1 mole % based on the combined amounts of mono- and bis-esters; and
    (c) removing additional unreacted aryloxyalkanol to provide a purified bis(aryloxyalkyl)terephthalate having an overall purity of at least 98 mole % and a yellowness index less than 10;
    wherein at least steps (a) and (b) are performed substantially in the absence of oxygen.

2. The process of claim 1 wherein the aryloxyalkanol has a boiling point at atmospheric pressure greater than 210° C.

3. The process of claim 1 wherein the aryloxyalkanol is 2-phenoxyethanol and the bis(aryloxyalkyl)terephthalate is bis(2-phenoxyethyl)terephthalate (PEM).

4. The process of claim 1 wherein from 2.0 to 2.8 molar equivalents of the aryloxyalkanol are used in step (a).

5. The process of claim 1 wherein from 70 to 80 mole % of the dimethyl terephthalate is converted to the bis(aryloxyalkyl)terephthalate in step (a).

6. The process of claim 1 wherein the catalyst comprises titanium or zirconium.

7. The process of claim 1 wherein the catalyst comprises zinc.

8. The process of claim 1 wherein the purified bis(aryloxyalkyl)terephthalate has a yellowness index less than 5.

9. The process of claim 1 wherein the purified bis(aryloxyalkyl)terephthalate has an overall purity of at least 99 mole %.

10. The process of claim 1 wherein the unreacted aryloxyalkanol is removed in step (b) with a gas or vapor purge.

11. The process of claim 1 wherein step (b) is performed at a temperature within the range of 175° C. to 230° C.

12. The process of claim 1 wherein the unreacted aryloxyalkanol is removed in step (c) under reduced pressure with a gas or vapor purge.

13. The process of claim 1 wherein the unreacted aryloxyalkanol is removed in step (c) by fractional melt or solvent crystallization.

14. The process of claim 1 further comprising pelletizing, flaking, granulating, pastillating, prilling, or spray drying the purified bis(aryloxyalkyl)terephthalate.

15. The process of claim 14 performed in the presence of PET.

16. The process of claim 1 wherein the purified bis(aryloxyalkyl)terephthalate is treated with an adsorbent to further reduce its yellowness index.

17. The process of claim 16 wherein the adsorbent is magnesium silicate.

18. A process for making a bis(aryloxyalkyl)terephthalate suitable for use as an antiplasticizer for polymers, comprising the steps of:
    (a) reacting dimethyl terephthalate with an excess of an aryloxyalkanol in the presence of a condensation catalyst comprising a Group 3, 4, 12, 13, 14, or 15 metal at a temperature less than the boiling point of the aryloxyalkanol to produce an intermediate mixture comprising a bis(aryloxyalkyl)terephthalate, a mono(aryloxyalkyl)terephthalate, and unreacted aryloxyalkanol;
    (b) continuing to react the intermediate mixture at a temperature within the range of 150° C. to 250° C. under reduced pressure while removing unreacted aryloxyalkanol and reducing the mono(aryloxyalkyl)terephthalate content of the mixture to less than 1 mole % based on the combined amounts of mono- and bis-esters;

(c) removing additional unreacted aryloxyalkanol to provide a purified bis(aryloxyalkyl)terephthalate having an overall purity of at least 98 mole % and a yellowness index less than 10; and (d) treating the purified bis(aryloxyalkyl)terephthalate with an adsorbent to further reduce its yellowness index;

wherein at least steps (a) and (b) are performed substantially in the absence of oxygen.

19. The process of claim 18 wherein the adsorbent is magnesium silicate.

20. A process for making a bis(aryloxyalkyl)terephthalate suitable for use as an antiplasticizer for polymers, comprising the steps of:

(a) reacting dimethyl terephthalate with an excess of an aryloxyalkanol in the presence of a condensation catalyst comprising zinc at a temperature less than the boiling point of the aryloxyalkanol to produce an intermediate mixture comprising a bis(aryloxyalkyl) terephthalate, a mono(aryloxyalkyl)terephthalate, and unreacted aryloxyalkanol;

(b) continuing to react the intermediate mixture at a temperature within the range of 150° C. to 250° C. under reduced pressure while removing unreacted aryloxyalkanol and reducing the mono(aryloxyalkyl)terephthalate content of the mixture to less than 1 mole % based on the combined amounts of mono- and bis-esters; and (c) removing additional unreacted aryloxyalkanol to provide a purified bis(aryloxyalkyl)terephthalate having an overall purity of at least 95 mole % and a yellowness index less than 10;

wherein at least steps (a) and (b) are performed substantially in the absence of oxygen.

21. The process of claim 20 wherein from 1.9 to 3.0 molar equivalents of the aryloxyalkanol are used in step (a).

22. The process of claim 20 wherein from 70 to 80 mole % of the dimethyl terephthalate is converted to the bis(aryloxyalkyl)terephthalate in step (a).

23. A process for making a bis(aryloxyalkyl)terephthalate suitable for use as an antiplasticizer for polymers, comprising the steps of:

(a) reacting dimethyl terephthalate with an excess of an aryloxyalkanol in the presence of a condensation catalyst comprising a Group 3, 4, 12, 13, 14, or 15 metal at a temperature less than the boiling point of the aryloxyalkanol to produce an intermediate mixture comprising a bis(aryloxyalkyl)terephthalate, a mono(aryloxyalkyl) terephthalate, and unreacted aryloxyalkanol wherein from 65 to 85 mole % of the dimethyl terephthalate is converted to said bis(aryloxyalkyl)terephthalate and 15 to 35 mole % of the dimethyl terephthalate is converted to said mono(aryloxyalkyl)terephthalate;

(b) continuing to react the intermediate mixture at a temperature within the range of 150° C. to 250° C. under reduced pressure while removing unreacted aryloxyalkanol and reducing the mono(aryloxyalkyl)terephthalate content of the mixture to less than 1 mole % based on the combined amounts of mono- and bis-esters; and (c) removing additional unreacted aryloxyalkanol to provide a purified bis(aryloxyalkyl)terephthalate having an overall purity of at least 98 mole % and a yellowness index less than 10;

wherein at least steps (a) and (b) are performed substantially in the absence of oxygen.

24. The process of claim 23 wherein from 1.9 to 3.0 molar equivalents of the aryloxyalkanol are used in step (a).

25. The process of claim 23 wherein from 70 to 80 mole % of the dimethyl terephthalate is converted to the bis(aryloxyalkyl)terephthalate in step (a).

26. The process of claim 23 wherein the purified bis(aryloxyalkyl)terephthalate has an overall purity of at least 99 mole %.

27. The process of claim 23 wherein the unreacted aryloxyalkanol is removed in step (b) with a gas or vapor purge.

28. The process of claim 23 wherein step (b) is performed at a temperature within the range of 175° C. to 230° C.

29. The process of claim 23 wherein the unreacted aryloxyalkanol is removed in step (c) under reduced pressure with a gas or vapor purge.

30. The process of claim 23 wherein the unreacted aryloxyalkanol is removed in step (c) by fractional melt or solvent crystallization.

* * * * *